(12) United States Patent
Zastrozna (10) Patent No.: US 9,877,786 B2
(45) Date of Patent: Jan. 30, 2018

(54) MODULAR NAVIGABLE PROBE

(71) Applicant: Stryker European Holdings I, LLC, Kalamazoo, MI (US)

(72) Inventor: Anna Zastrozna, Teaneck, NJ (US)

(73) Assignee: Stryker European Holdings I, LLC, Kalamazoo, MI (US)

( * ) Notice: Subject to any disclaimer, the term of this patent is extended or adjusted under 35 U.S.C. 154(b) by 663 days.

(21) Appl. No.: 14/196,514

(22) Filed: Mar. 4, 2014

(65) Prior Publication Data

US 2014/0257332 A1 Sep. 11, 2014

Related U.S. Application Data (60) Provisional application No. 61/773,375, filed on Mar. 6, 2013.

(51) Int. Cl.
  *A61B 90/10* (2016.01)
  *A61B 19/00* (2006.01)
  (Continued)

(52) U.S. Cl.
  CPC .......... *A61B 19/20* (2013.01); *A61B 17/1703* (2013.01); *A61B 17/1757* (2013.01);
  (Continued)

(58) Field of Classification Search
  CPC ........ A61B 17/3421; A61B 2017/3443; A61B 2017/3447; A61B 2017/347; A61B 2017/348
  (Continued)

(56) References Cited

U.S. PATENT DOCUMENTS 7,166,114 B2 1/2007 De La Barrera et al.
7,987,001 B2 7/2011 Teichman et al.
(Continued)

FOREIGN PATENT DOCUMENTS

DE 19831835 A1 1/2000
JP 2007508050 A 4/2007
(Continued)

OTHER PUBLICATIONS

Brainlab, "Confident Placement: Navigated Pedicle Access Needle", 2 pages, Copyright 2013.
(Continued)

*Primary Examiner* — Tuan V Nguyen
*Assistant Examiner* — Chima Igboko
(74) *Attorney, Agent, or Firm* — Lerner, David, Littenberg, Krumholz & Mentlik, LLP (57) ABSTRACT

A navigable probe system and method of use is provided. The system may include a handle assembly having a locking mechanism enclosed and a stylus, a cannula, and a tracking device extending from the handle assembly. The stylus may include undercuts for receiving pins of the locking mechanism. A cam of the handle assembly may rotate such that in a first position, the pins of the locking mechanism may be engaged with the undercuts and in a second position, the pins of the locking mechanism may be disengaged from the undercuts releasing the stylus from the locking mechanism. The stylus may be slidably engaged with an inner diameter of the cannula. In some arrangements, the handle assembly may include a quick connect system that in a first position attaches the cannula to the handle assembly and in a second position releases the handle assembly and thus stylus from the cannula.

15 Claims, 6 Drawing Sheets

(51) Int. Cl.
*A61B 17/17* (2006.01)
*A61B 17/34* (2006.01)
*A61B 34/20* (2016.01)
*A61B 17/00* (2006.01)
*A61B 90/00* (2016.01)

(52) U.S. Cl.
CPC .......... *A61B 17/3421* (2013.01); *A61B 34/20* (2016.02); *A61B 90/10* (2016.02); *A61B 2017/00039* (2013.01); *A61B 2017/347* (2013.01); *A61B 2090/062* (2016.02); *A61B 2090/3983* (2016.02); *Y10T 29/4973* (2015.01)

(58) Field of Classification Search
USPC .................................................. 81/124.5, 126
See application file for complete search history.

(56) References Cited

U.S. PATENT DOCUMENTS

| | | | | |
|---|---|---|---|---|
| 2004/0054489 | A1* | 3/2004 | De La Barrera | G06F 19/327 |
| | | | | 702/105 |
| 2006/0173521 | A1 | 8/2006 | Pond et al. | |
| 2007/0010843 | A1* | 1/2007 | Green | A61B 10/0233 |
| | | | | 606/185 |
| 2007/0088277 | A1* | 4/2007 | McGinley | A61B 17/3462 |
| | | | | 604/167.01 |
| 2007/0260184 | A1* | 11/2007 | Justis | A61B 17/16 |
| | | | | 604/164.01 |
| 2008/0228195 | A1 | 9/2008 | Von Jako et al. | |
| 2011/0251597 | A1 | 10/2011 | Bharadwaj et al. | |
| 2011/0301593 | A1 | 12/2011 | Teichman et al. | |

FOREIGN PATENT DOCUMENTS

| | | |
|---|---|---|
| JP | 2009535181 A | 10/2009 |
| WO | 9304717 A1 | 3/1993 |
| WO | 9601074 A2 | 1/1996 |
| WO | 2005039430 A2 | 5/2005 |
| WO | 2006017507 A2 | 2/2006 |

OTHER PUBLICATIONS

Brainlab, "Spine Navigation", 19 pages, Copyright 2013.
Extended European Search Report for Application No. EP14158045 dated Jun. 27, 2014.
Medtronic, "Navigated PAK Needle: Pedicle Access Kit for Synergy® Spine Navigation", 2 pages, Copyright 2009.
Viper, "Surgical Technique & Product Catalogue: Guide for Open & MIS Procedures", 11 pages, DePuy Spine, Inc., Copyright 2011.

* cited by examiner

MODULAR NAVIGABLE PROBE

CROSS-REFERENCE TO RELATED APPLICATION

The present application claims the benefit of the filing date of U.S. Provisional Application No. 61/773,375, filed Mar. 6, 2013, the disclosure of which is hereby incorporated herein by reference.

BACKGROUND OF THE INVENTION

The present invention relates to systems and methods for pedicle screw insertion into a spine, and in particular, to navigational probes for creating a trajectory in a pedicle for subsequent pedicle screw insertion.

Various systems have been developed to aid surgeons in translating and tracking the position of surgical tools or probes during surgical procedures, such as the system described in U.S. Pat. No. 7,166,114 ("the '114 patent"), the entire disclosure of which is hereby incorporated by reference herein. Such systems have been useful in performing neurological related procedures such as procedures for insertion of pedicle screw into the spines of patients. A navigable jamshidi and certain custom probe designs have been used to perform such steps of these procedures. However, these devices frequently lose positions registered by the navigation tracking system that interfaces with the devices, often due to unreliable attachment of an adapter connecting the navigation tracking system to the devices which leads to undesirable rotational movement of the navigation tracking system. As such, these probe devices require calibration of both position and orientation with respect to the tracking systems with which they are used. Furthermore, custom probe designs often have a stylus tip that is difficult to remove from bone upon insertion and, moreover, jamshidis have a relatively small cannula diameter which makes them prone to permanent bending and lodging in the bone when used with navigable probe devices.

Other systems having navigable disposable needles that may be used with dedicated, often permanently attached tracking systems and those having rigid cannulated probes or jamshidis, require separate instruments to perform various steps of surgical procedures in which these systems are used. For instance, such systems may require a slim dilator to initiate uniform expansion of an incision prior to using another larger dilator. When calibrating a navigable probe device having either an adapter for attaching or when permanently attaching a navigation tracking system to a probe, separate calibration of additional navigable instruments is required to be used during the surgical procedure.

Thus, there is a need for a navigable probe that can be used to perform multiple surgical steps and that is modular to allow for separation of a handle from any of a stylus and a cannula. There is a further need for a navigable probe having a fixed portion relative to a tracking system used therewith which maintains the registry after replacement of one or both of the stylus and cannula without the need to recalibrate in order to prevent unreliable registry of probe positions.

SUMMARY OF THE INVENTION

In an aspect of the disclosure, a navigable probe is provided. The navigable probe may include a handle assembly. The handle assembly may include a lower handle. The handle assembly may include an upper cap assembly that may include an upper cap and that may include a cam fixed to the upper cap. The upper cap assembly may be rotatable relative to the lower handle. The handle assembly may include a handle base assembly that may include inner and outer tubes. The inner tube may have a flat portion that may be along an inner perimeter of a proximal portion of the inner tube.

The handle assembly may include a locking mechanism that may be enclosed by the upper cap assembly and the lower handle. The locking mechanism may include an impaction cap that may be inserted into a base. The locking mechanism may include one or more pins that may be inserted through the base and the impaction cap. The locking mechanism may include a leaf spring that may be fixedly attached to each of the pins.

The navigable probe may include a stylus. The stylus may have a proximal end in which the proximal end may include opposing flats. The stylus may include a distal end. The stylus may include opposing undercuts that may be sized to receive a diameter of the respective pins of the locking mechanism. The proximal end of the stylus may be insertable through a portion of an inner diameter of the impaction cap. The proximal end of the stylus may be insertable through the proximal portion of an inner diameter of the inner tube of the handle base assembly. The distal end of the stylus may be insertable through an inner diameter of a cannula. The proximal end of the stylus may have a protrusion extending from a distal portion of the proximal end of the stylus.

The navigable probe may include a cannula. The cannula may have a proximal end that may include opposing flats and a recess. The recess may receive the protrusion of the stylus. The cannula may be insertable through the handle assembly, and in some arrangements, through a second portion of the inner diameter of the inner tube of the handle base assembly. The cannula may include a taper between a first portion of the cannula having a first outer diameter and a second portion of the cannula having a second outer diameter that may be smaller than the first diameter. The cannula may include depth markings for determining a depth of insertion of the cannula. The cannula may include a dielectric material that may aide in neuromonitoring.

The navigable probe may include a quick connect system. The quick connect system may include a collar that may be slidable in a direction parallel to a longitudinal axis of the cannula. In this manner, sliding the collar towards the handle assembly may cause a spring of the quick connect system to be compressed between the collar and the outer tube of the handle base assembly. The collar may have a taper. In this manner, a ball compressed between the collar and the cannula may change from a compressed state to a relaxed state.

The navigable probe may include a tracking arm that may be attachable to and that may be extendable from the first outer diameter of the cannula. The tracking arm may include a flat portion on an end adjacent to the first outer diameter of the cannula. The tracking arm may include tracker posts extending from an opposite end of the tracking arm.

The navigable probe may include a tracking module that may be attachable to the tracker posts of the tracking arm. The tracking module may include a navigation system for monitoring and displaying the position of the stylus. Upon rotation of the cam of the upper cap assembly of the handle assembly to a locked position, portions of the cam may press the one or more pins of the locking mechanism into the respective opposing undercuts of the stylus. In this manner, axial movement of the stylus may be prevented. Upon rotation of the cam to an unlocked position, the leaf spring that may correspond to each pin may supply a force that may retract the respective pin from the respective undercut.

The flats of the stylus and the cannula may correspond to the flat portions of the inner tube. In this manner, when the cannula and the stylus are seated in the inner tube, planes through each of the flats of the stylus and the flats of the cannula may be parallel. In this manner, the flats of the stylus and the cannula may be in mating engagement in which such mating engagement may prevent rotation of the cannula and may prevent rotation of the stylus relative to the handle assembly. In this manner, the undercuts of the stylus may be in alignment with the pins such that the pins may be inserted into the respective undercuts when the cam of the upper cap assembly is rotated to the locked position.

In an aspect of the disclosure, a method of replacing components of a modular navigable probe assembly is provided. The method may include rotating an upper cap assembly of a handle assembly relative to a handle base assembly of the handle assembly from a locked to an unlocked position. The upper cap assembly may include an upper cap and a cam that may be fixed to the upper cap. The handle assembly may include a lower handle. The handle assembly may include a handle base assembly. The handle base assembly may include an inner tube and may include an outer tube. The inner tube may include a flat portion along an inner perimeter of a proximal portion of the inner tube.

The handle assembly may include a locking mechanism. The locking mechanism may include an impaction cap. The first impaction cap may be inserted into a base that may rotate the same rotational angle as the upper cap assembly during rotation of the upper cap assembly. The locking mechanism may include one or more pins that may be inserted through the base and the impaction cap. The locking mechanism may include a resilient element. The resilient element may be fixedly attached to each of the pins.

The method of replacing components of a modular navigable probe assembly may include removing the upper cap assembly from the handle base assembly.

The method of replacing components of a modular navigable probe assembly may include sliding a collar of a quick connect system in a direction parallel to a longitudinal axis of a first cannula. The direction of sliding may be towards the handle assembly. The sliding may cause a spring of the quick connect system to be compressed between the collar and the outer tube of the handle base assembly. The collar may have a taper. In this manner, a ball compressed between the collar and the first cannula may change from a compressed state to a relaxed state. The first cannula may include a proximal end that may include opposing flats and that may include a recess. The first cannula may be insertable through a second portion of the inner diameter of the inner tube of the handle base assembly. The first cannula may include a taper between a first portion of the cannula having a first outer diameter and a second portion of the cannula having a second outer diameter that may be smaller than the first diameter. The first cannula may include depth markings for determining a depth of insertion of the first cannula. The first cannula may include a dielectric material for aiding in neuromonitoring.

The method of replacing components of a modular navigable probe assembly may include disconnecting the first cannula from the handle base assembly, such as after sliding the collar of the quick connect system, which may enable fluoroscopy along a longitudinal axis of the first cannula without radiopaque interference from the handle assembly.

The method of replacing components of a modular navigable probe assembly may include extracting a stylus from the handle assembly, such as after rotating the upper cap assembly from a locked to an unlocked position. The stylus may have a proximal end that may include opposing flats. The stylus may have a distal end. The stylus may include opposing undercuts sized to receive a diameter of the respective pins of the locking mechanism. When the upper cap assembly is in the unlocked position, the proximal end of the stylus may be insertable through a portion of an inner diameter of the impaction cap and may be insertable through the proximal portion of an inner diameter of the inner tube of the handle base assembly. When the upper cap assembly is in the unlocked position, the distal end of the stylus may be insertable through an inner diameter of the first cannula. The proximal end of the stylus may have a protrusion. The protrusion may extend from a distal portion of the proximal end of the stylus. In this manner, the protrusion of the stylus may be inserted into the recess of the first cannula.

The method of replacing components of a modular navigable probe assembly may include placing a second cannula over a first diameter of the first cannula, such as after the step of disconnecting the first cannula from the handle base assembly. The first diameter of the first cannula may be substantially equal but less than a second diameter of the second cannula that surrounds the first diameter of the first cannula upon placement of the second cannula over the first cannula.

The method of replacing components of a modular navigable probe assembly may include connecting the first cannula to the handle assembly, such as after the step of extracting the stylus, to aid in cannula removal from the bone.

The method of replacing components of a modular navigable probe assembly may include connecting to the handle assembly, such as after the step of disconnecting at least one of the stylus and the cannula, any of at least one of a drill guide, a drill, an awl, a neuromonitoring probe that may include leads, an ultrasound probe, a bone aspiration and cement delivery needle, a probe-specific cannula, a needle-specific cannula, end plate preparation instruments, and interbody device insertion instruments.

In an aspect of the disclosure, a navigable probe is provided. The navigable probe may provide a trajectory for insertion of surgical tools. The navigable probe may track the position of the surgical tools. The navigable probe may include a handle assembly. The navigable probe may include a cannula. The cannula may be disposed within and may be removably connected to the handle assembly. The navigable probe may include a stylus. The stylus may be disposed within the cannula and may be removably connected to the handle assembly.

In some arrangements, the navigable probe may include a tracking module. The tracking module may be connected to the handle assembly. The tracking module may be fixed in position relative to at least one of the cannula and the stylus. The tracking module may detect at least one of position and orientation of the navigable probe.

In some arrangements, the tracking module may be connected to the handle assembly by an arm. An impaction surface of the arm may be flat. The impaction surface may provide for an impaction force over an area of the impaction surface against a body tissue, such as during removal of the cannula from the handle assembly.

In some arrangements, the handle assembly may include a locking mechanism having locked and unlocked positions. In the locked position, the locking mechanism may engage the stylus to prevent axial movement of the stylus relative to the handle assembly. In the unlocked position, the locking mechanism may disengage the stylus. In this manner, the locking mechanism may allow for axial movement of the stylus relative to the handle assembly.

In some arrangements, in the locked position of the locking mechanism, one or more pins of the locking mechanism may be disposed in corresponding undercuts defined by the stylus. In some arrangements, in the unlocked position of the locking mechanism, the one or more pins of the locking mechanism may not be disposed in the corresponding undercuts defined by the stylus.

In some arrangements, the navigable probe may include a quick connect system. In some arrangements, the quick connect system may be removably fixed to the cannula to the handle assembly. The quick connect system may be adjustable between first and second positions. When the quick connect system is in the first position, the cannula may be fixed in position relative to the handle assembly. When the quick connect system is in the second position, the cannula may be movable relative to the handle assembly.

In some arrangements, the cannula and the stylus may be slideably engaged with each other. When the quick connect system is in the first position, the cannula may be fixed in position relative to the stylus. When the quick connect system is in the second position, the stylus may be slideable along the cannula.

In some arrangements, the handle assembly may include a locking mechanism having locked and unlocked positions. In the locked position, the locking mechanism may engage the stylus to prevent axial movement of the stylus relative to the handle assembly. In the unlocked position, the locking mechanism may disengage the stylus to allow for axial movement of the stylus relative to the handle assembly. In some arrangements in which the quick connect system is in the second position and the locking mechanism is in the unlocked position, both the handle assembly and the stylus may be removable from the cannula.

In some arrangements, the handle assembly and the stylus may be fixed to each other such that the stylus is not axially movable relative to the handle assembly.

In some arrangements, the quick connect system may include a collar. The collar may have at least a portion that is movable between first and second positions that may be along a portion of the handle assembly in a direction parallel to a longitudinal axis of the cannula. The quick connect system may include a compression element that may be compressible between the handle assembly and the collar. The quick connect system may include a locking element. In some such arrangements, the locking element may be held between the collar and the cannula. When the collar is in a first position, the compression element may compress the collar against the locking element. In this manner, the locking element may be compressed against the cannula such that the position of the cannula relative to the handle assembly is fixed. When the collar is in the second position, the locking element may be placed in a state such that the handle assembly and the cannula are slideable relative to each other.

In some arrangements, the collar may have a taper such that, when the collar is in the first position, the taper may contact the locking element. Such contact may cause compression of the cannula and may maintain the position of the cannula relative to the handle assembly.

In some arrangements, the locking element may be ball-shaped.

In some arrangements, the handle assembly may include a lower handle. In some arrangements, the handle assembly may include an upper cap assembly. The upper cap assembly may include an upper cap and a cam that may be fixed to the upper cap. The cam may be rotatable relative to the lower handle.

In some arrangements, the handle assembly may include a locking mechanism. The locking mechanism may be enclosed by the upper cap assembly and the lower handle. The locking mechanism may include one or more pins that may be insertable into a proximal end of the stylus. The locking mechanism may include a resilient element. The resilient element may be attached to the pins of the locking mechanism. Upon rotation of the upper cap assembly to a locked position, the cam may press at least a portion of one or more of the pins into the proximal end of the stylus such that the stylus may be fixed in position relative to the handle assembly. Upon rotation of the upper cap assembly to an unlocked position, the resilient element may supply a force against one or more of the pins such that the pins are retracted from the stylus.

In some arrangements, the resilient element may be a leaf spring. The leaf spring may be compressed between flanges extending radially from each of the pins. In this manner, the leaf spring may supply a force to the flanges of the pins.

In some arrangements, the handle assembly may include at least one tube extending along a distal portion of the handle assembly. The one or more tubes may extend coaxially with the cannula and the stylus passing through a lumen defined by the one or more tubes. The stylus may include at least one flat stylus surface at a proximal end of the stylus. The cannula may include at least one flat cannula surface at a proximal end of the cannula. One or more of the tubes may have at least one flat inner surface along at least a portion of one or more of the tubes for mating engagement with each of the flat stylus surface and the flat cannula surface. In this manner, when the flat stylus surface and the flat cannula surface are in mating engagement, rotation of at least one of the cannula and the stylus relative to the handle assembly may be prevented.

In an aspect of the disclosure, a method for replacing components of a modular navigable probe assembly is provided. The method may include rotating a first subassembly of a handle assembly relative to a second subassembly of the handle assembly. The rotation of the first subassembly relative to the second subassembly may be from a first position to a second position. In the first position, the stylus may be locked to the handle assembly. In the second position, the stylus may be removable from the handle assembly.

The method for replacing components of a modular navigable probe assembly may include moving a collar of a quick connect system. The collar may be moved along a portion of the handle assembly from a first position to a second position. In the first position of the collar, the cannula may be locked to the handle assembly. In the second position, the cannula may be removable from the second subassembly of the handle assembly.

In some arrangements, the stylus may be slideably received in the cannula.

In some arrangements, the method may include removing the handle assembly from both the stylus and the cannula, such as when both the first subassembly of the handle assembly is rotated to the second position of the first subassembly and the collar of the quick connect system is moved to the second position of the collar.

In some arrangements, the method may include, after removal of at least one of the stylus and the cannula, receiving in the handle assembly any of at least one of a drill guide, a drill, an awl, a neuromonitoring probe including leads, an ultrasound probe, a bone aspiration and cement delivery needle, a probe-specific cannula, a needle-specific cannula, end plate preparation instruments, and interbody device insertion instruments.

In some arrangements, the handle assembly may include a locking mechanism. The locking mechanism may be attached to the second subassembly of the handle assembly. The first subassembly of the handle assembly may include a cam fixed to the first subassembly. The locking mechanism may include one or more pins. The pins may be insertable into a proximal end of the stylus. A resilient element may be attached to the pins of the locking mechanism. When the first subassembly is in the first position of the first subassembly, the cam may press against at least a portion of the pins such that the pins may be inserted into the proximal end of the stylus. In this manner, the stylus may be fixed in position relative to the handle assembly. When the first subassembly is in the second position of the first subassembly, the resilient element may supply a force against the pins such that the pins may be retracted from the stylus.

DETAILED DESCRIPTION

Where reference is made herein to directional terms such as "proximal," "proximal most," "distal," and "distal most," it is to be understood that "proximal" and "proximal most" refer to locations closer to a user or operator of the device or method being described and that "distal" and "distal most" refer to locations further from a user or operator of the device or method being described.

Figure 1:
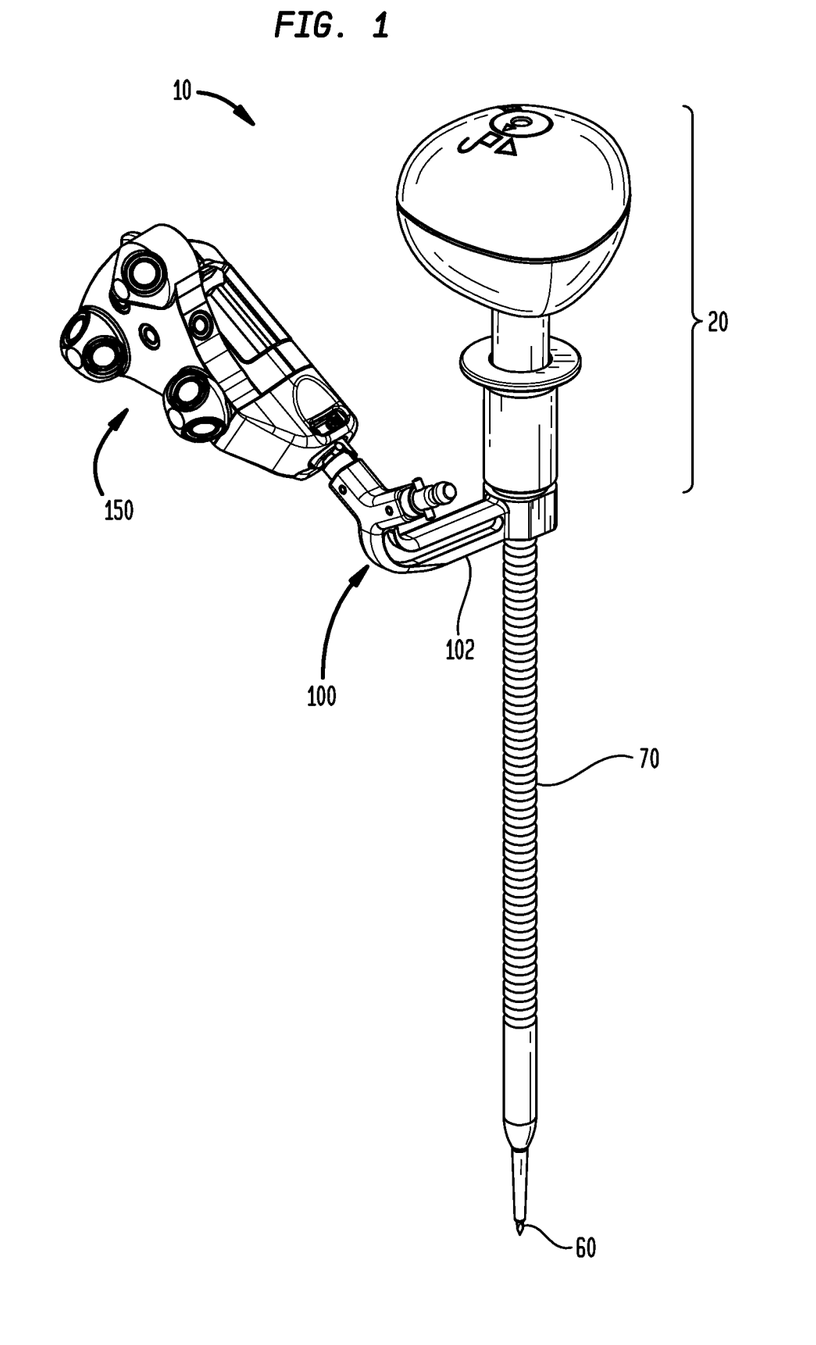
FIG. 1 is a perspective view of a navigable probe assembly in accordance with an embodiment.

Referring to FIG. 1, a navigable probe assembly 10 according to one embodiment may include a handle assembly 20 attached to a tracker arm 100 as well as a stylus 60 concentrically inserted into a cannula 70. A portion of each of the stylus 60 and cannula 70 may be disposed within the handle assembly 20. As shown, a tracking module 150 may be attached to a connector extending from the tracker arm 100.

Figure 2:
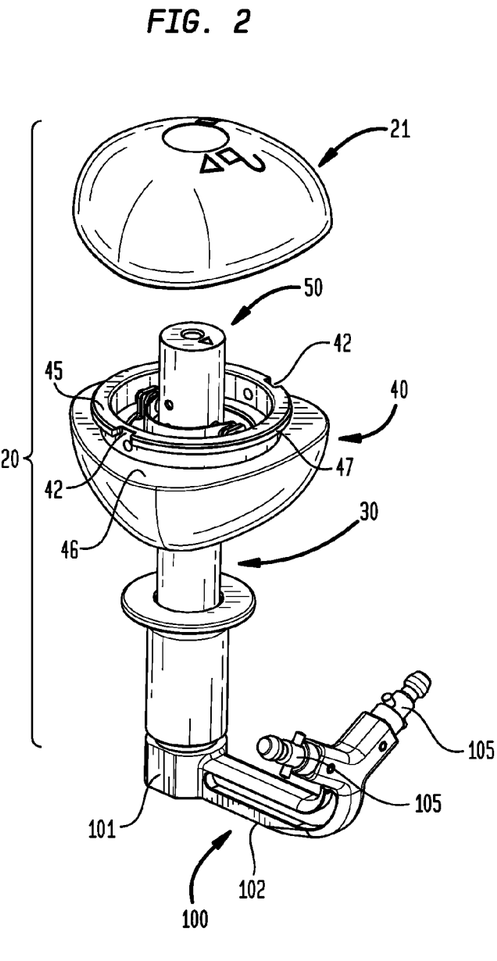
FIG. 2 is a partial exploded and partial perspective view of a portion of the navigable probe assembly of FIG. 1.
Figure 3:
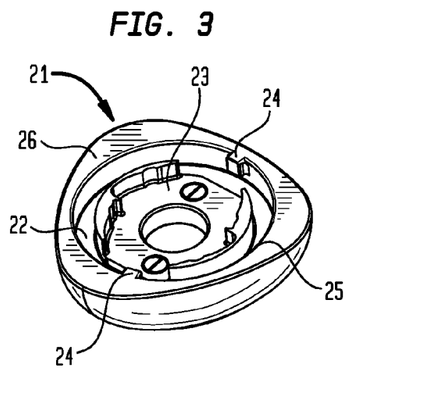
FIG. 3 is a perspective view of an upper cap assembly of the navigable probe assembly of FIG. 1.
Figure 6:
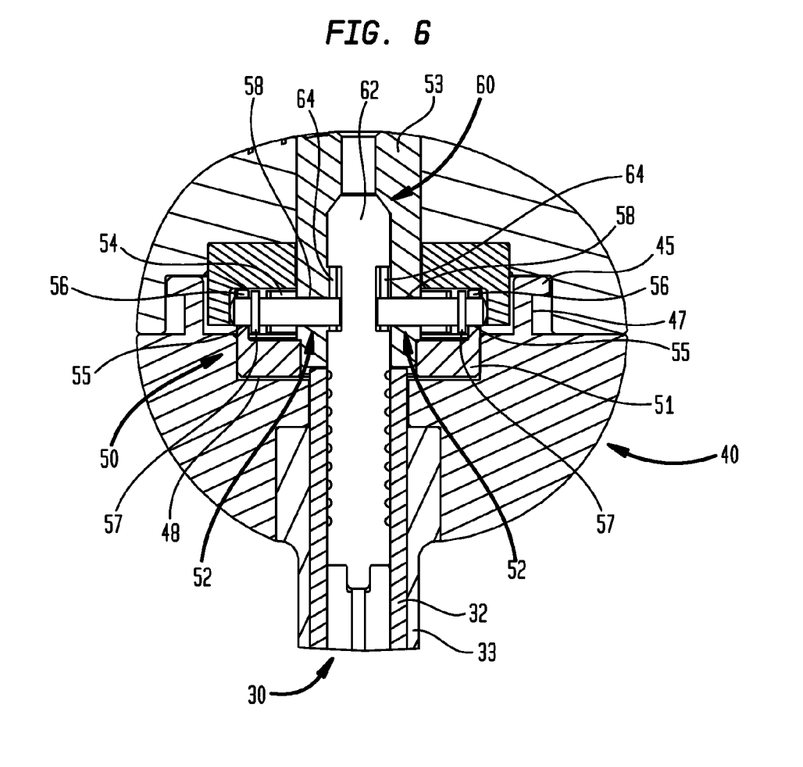
FIG. 6 is a cross-sectional front side view of a portion of the navigable probe assembly of FIG. 1.

As illustrated in FIG. 2, the handle assembly 20 includes an upper cap assembly 21, a handle base assembly 30 (described further below), a locking mechanism 50, and a lower handle 40 that in conjunction with the upper cap assembly 21 enclose a portion of the handle base assembly 30 and the locking mechanism 50. As shown in FIG. 3, a cam 23 may be inserted into a cavity 22 of the upper cap assembly 21 (as best shown in FIG. 6) and fixed to the upper cap assembly 21. As shown, in some arrangements, the cam 23 is fixed by a screw to the upper cap assembly 21. In other arrangements (not shown), the cam 23 may be fixed to the upper cap assembly 21 by, but not limited to, bonding the cam 23 to the upper cap assembly 21 using an adhesive, such as epoxy, or by forming the cam 23 and the upper cap assembly 21 as a unitary body, such as by net-shape injection molding or by cutting of a solid block.

The upper cap assembly 21 may include at least two tabs 24 extending from opposing positions around an inner perimeter 25 of the upper cap assembly 21 as well as a flat lower surface 26. The lower handle 40 may include at least two recesses 42 within a boss 45 extending from a flat upper surface 46 of the lower handle 40 and having a boss undercut (as best shown in FIG. 6) around a perimeter of the boss 45. The recesses 42 may be located at positions around the boss 45 corresponding to the positions of the tabs 24. Thus, there may be at least as many recesses 42 as there are tabs 24 formed in such a configuration. The tabs 24 of the upper cap assembly 21 may be inserted into the recesses 42 of the lower handle 40, and the upper cap assembly 21 and the lower handle 40 may be rotated relatively to one another as the tabs 24 slide within and around the boss undercut 47. In some arrangements (not shown), the tabs and the boss may be reversed such that the tabs may be attached to the lower handle and the boss may extend from the upper cap assembly.

The upper cap assembly 21 and the lower handle 40 may have corresponding shapes such that upon their relative rotation, the upper cap assembly 21 and the lower handle 40 may be locked together, and the flat lower surface 26 of the upper cap assembly 21 and the flat upper surface 46 of the lower handle 40 may rest flush against each other around respective perimeters of these surfaces. The ability to engage and disengage the upper cap assembly 21 and the lower handle 40 may allow for cleaning debris out of an interior of the handle assembly 20. In some arrangements, such as shown in FIG. 2, the upper cap assembly 21 and the lower handle 40 may have smooth and rounded exteriors that provide for a more ergonomic surface for handling by a user of the navigable probe assembly 10. As shown, the upper cap assembly 21 and the lower handle 40 may have a hard or rigid shell that allows for the reuse thereof in subsequent surgical procedures.

Figure 4A:
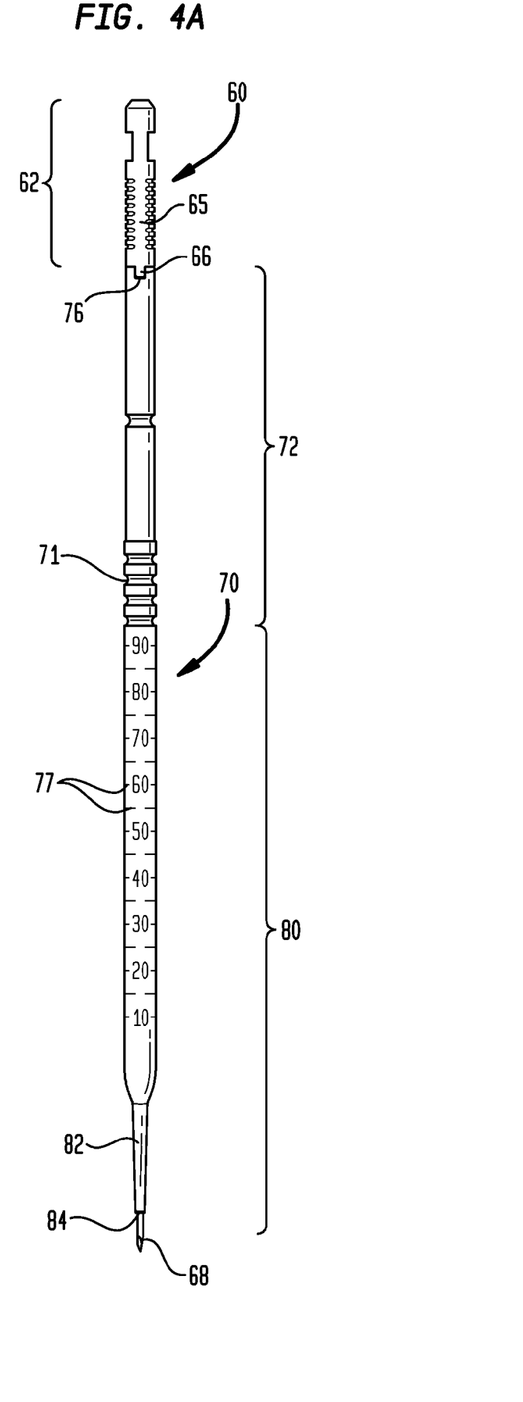
FIGS. 4(A) and 4(B) are perspective views of arrangements of assemblies of styli and cannulae for use with a navigable probe assembly in accordance with certain embodiments.
Figure 4B:
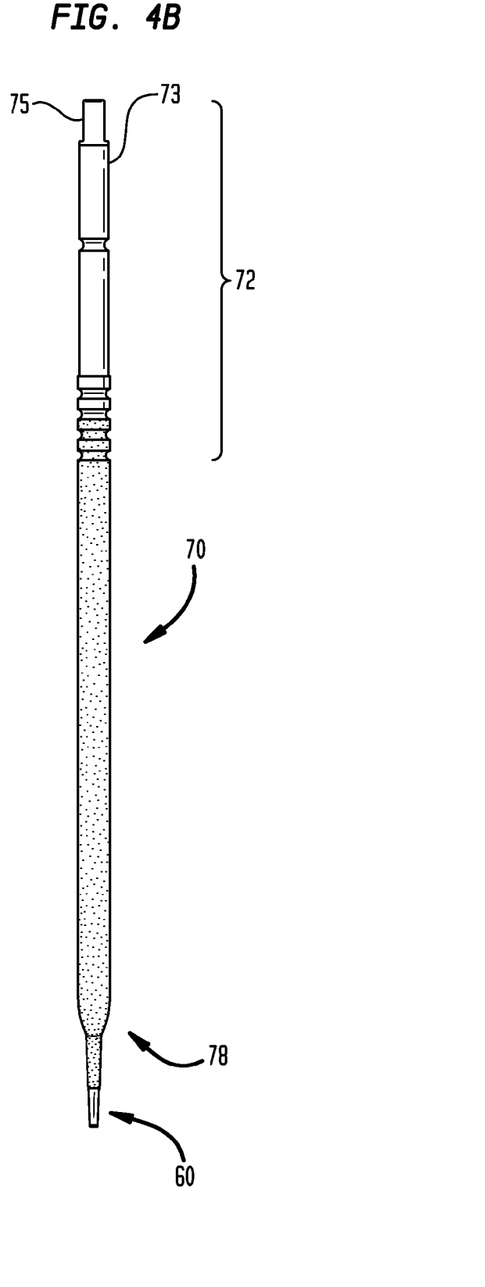

As shown in FIGS. 4A and 4B, the stylus 60 includes a proximal end 62 having a stylus undercut 64 for connection with the handle base assembly 30 on a first portion of the proximal end 62, as discussed further down below, and a protrusion 66 for connection with a proximal end 72 of the cannula 70. The stylus 60 further includes a distal end 68 having an outer diameter sized to pass through an inner diameter of the cannula 70 and having a sharp tip that acts in a similar manner to a trochar, such as known by those of ordinary skill in the art. As further shown in FIG. 4A, the proximal end 72 of the cannula 70 may have a recess 76 for receiving the protrusion 66 of the stylus 60. Stylus flats 65 and cannula flats 75 may be formed on the respective proximal ends 62, 72 of the respective stylus 60 and cannula 70 for aiding in alignment with flats on the tracker arm 100, as described further below. These flats aid in preventing rotation of the stylus 60 and the cannula 70 to allow for easier insertion of these components into bone.

As further shown in FIG. 4A, in some arrangements, depth markings 77 may be included on a distal end 80 of the cannula 70. Also, in some arrangements as shown, the cannula may include grooves 71 along a central portion of the cannula 70 to provide a hand grip to ease the assembly and disassembly of the probe assembly 10 and to allow the cannula to be pulled out of bone, such as a pedicle, in instances in which the cannula is not lodged in the bone. As further shown in FIG. 4B, in some arrangements, a dielectric coating 78 may be added to the distal end 80 of the cannula 70 which may be used when the cannula 70 is used as part of a neuromonitoring procedure known to those of ordinary skill in the art. As shown in FIGS. 4A and 4B, in some arrangements, a more proximal portion of the distal end 80 of the cannula 70 may have a larger diameter than a distal most portion 82 of the cannula 70, which may be tapered, such that the cannula 70 may act as a dilator of the soft tissue in place of an initial dilator traditionally used for dilating the soft tissue in a separate step of the procedure. In some arrangements, the cannula 70 may include a tapered tip 84 that may serve as a jamshidi to further facilitate insertion of the cannula 70 into bone and to maximize the stiffness at the distal end of the probe assembly 10.

Figure 5:
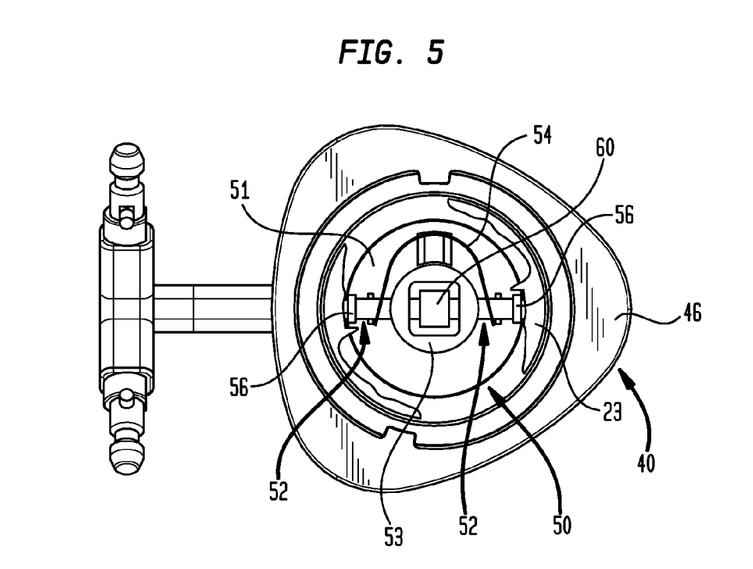
FIG. 5 is a plan view of the navigable probe assembly of FIG. 1 in which the upper cap assembly has been removed.

As illustrated in FIGS. 5 and 6, the locking mechanism 50 includes a base 51, pins 52, impaction cap 53, and resilient element 54. The pins 52 may be inserted on an outer end through holes 55 within protruding stands 56 on opposite sides of the base 51 and on an inner end through holes 58 extending radially through the impaction cap 53. The base 51 may be inserted into a cavity 48 of the lower handle 40. As illustrated, in some arrangements, the resilient element 54 may be a leaf spring that may be U-shaped. The resilient element 54 may be compressed between pin flanges 57 extending radially from a longitudinal axis of the pins 52. In an alternative arrangement (not shown), the resilient element may be a set of at least two coiled springs in which each of the coiled springs is compressed between the impaction cap 53 and the pin flanges 57. Although the base 51, the impaction cap 53, and the lower handle 40 are shown as separate components to allow easier access to clean these components, combinations of the base and the impaction cap, the base and the lower handle, as well as all of the base, the impaction cap, and the lower handle may be integrated such that any of these combinations of these structures may form a monolithic structure.

Figure 7:
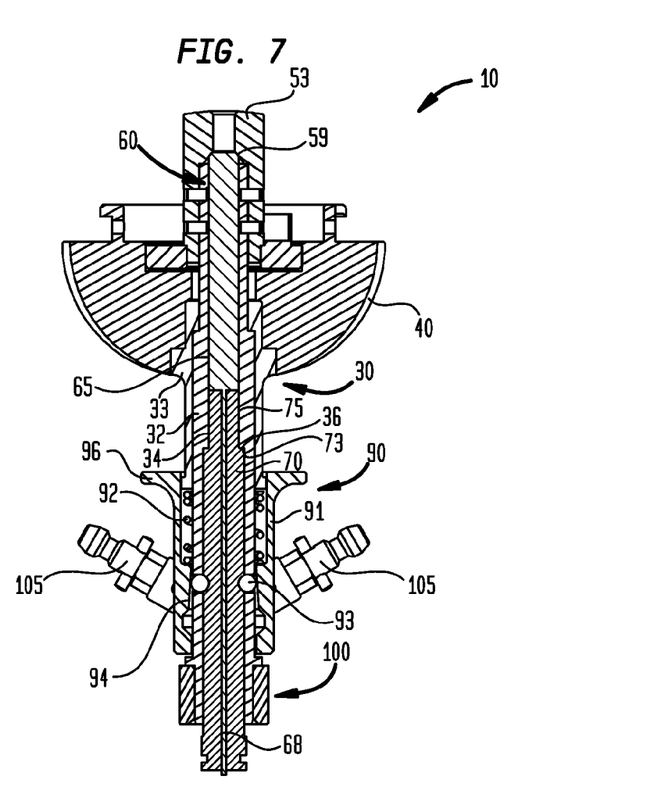
FIG. 7 is a cross-sectional rear side view of another portion of the navigable probe assembly of FIG. 1.

As illustrated in FIGS. 6 and 7, the handle base assembly 30 may be inserted into a distal portion of the lower handle 40. As shown, the handle base assembly 30 may include an inner tube 32 that extends from a distal end of the impaction cap 53 as well as an outer tube 33 and a quick connect system 90 that each surround and are coaxial with the inner tube 32. As shown in FIG. 7, the quick connect system 90 includes a collar 91 that surrounds the outer diameter of the inner tube 32 and that, when assembled, axially compresses a compression element 92, such as a compression spring, and radially compresses a locking element (or elements) 93, such as but not limited to balls or other objects with protruding features, to maintain an axial position of an object, such as the cannula 70 as described further herein, in contact with the locking element 93. To release the cannula 70, the collar 91 may be pushed axially to cause the compression element 92 that otherwise maintains the axial position of the collar 91 to be compressed against an end of the outer tube 33. As further shown in FIG. 7, the collar 91 has an inner diameter 94 around a circumference thereof that tapers in a direction away from the compression element 92 such that, upon axial movement of the collar 91 causing the compression element 92 to be compressed, the locking element 93 relaxes the compression force against the cannula 70. Upon relaxation of the compression force, the cannula 70 may then be displaced axially, and subsequently removed from an interconnection with another element, such as the inner tube 32 of the handle base assembly 30.

As best shown in FIG. 6, the stylus 60 may be placed within and the proximal portion 62 thereof may be slidingly engaged with an inner diameter of the impaction cap 53 and an inner diameter of the inner tube 32 of the handle base assembly 30. As shown in FIGS. 6 and 7, when the distal end of the stylus 60 is placed within the cannula 70, as described previously herein, the stylus 60 may be slidingly engaged with the inner diameter of the cannula 70. In this configuration, the outer diameter of the cannula 70 may be slidingly engaged with a portion of the inner tube 32 of the handle base assembly 30 that is distal to the portion of the inner tube 32 to which the stylus 60 is slidingly engaged.

Referring to FIG. 7, the inner tube 32 may include internal flats 34 on a proximal end thereof which mate to and engage with each of the respective stylus flats 65 and cannula 75 to prevent rotation of the stylus 60 and the cannula 70 at least when the stylus 60 and the cannula 70 are fully inserted in the inner tube 32. In this manner, torque may be transmitted through the navigable probe assembly, such as by a surgeon's hand, through the handle assembly to the cannula and the stylus during manipulation within bone. Moreover, preventing rotation of the stylus and cannula allows for setting of the position of the stylus 60 relative to the locking mechanism 50, and thus for the setting of the relative angular position of the stylus undercuts 64 to the pins 52 as described previously herein.

Figure 8:
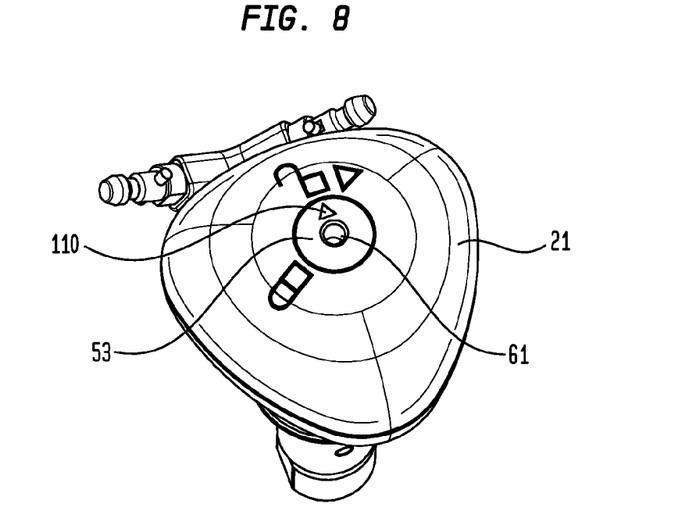
FIG. 8 is a perspective view of a handle assembly and a tracker arm of the navigable probe assembly of FIG. 1.

As illustrated in FIG. 8, the impaction cap 53 extends through the upper cap assembly 21 such that a proximal surface of the impaction cap 53 is exposed to a user. As shown, the impaction cap 53 is not fixed to the upper cap assembly 21 such that the upper cap assembly 21 may be rotated relative to the impaction cap 53 and lower handle 40. In this manner, an arrow 110 on the proximal surface of the impaction cap 53 may indicate when the upper cap assembly 21, and thus the cam 23, are positioned such that the pins 52 are within the stylus undercuts 64 and thus in a "locked position" or, in contrast, when the positions of these components are such that the pins 52 are not within the stylus undercuts 64 and thus in an "unlocked position". As shown, the impaction cap 53 may include an aperture 61 along a longitudinal axis of the cap. The aperture may permit insertion of instruments or portions of instruments therethrough, such as those described further herein.

As shown in FIGS. 1, 2, and 7, the tracker arm 100 may be attached on one end thereof to the inner tube 32 and extend radially and upwardly from the point of attachment. Such an attachment may be by an interference fit between an outer diameter of the inner tube 32 and an inner diameter of a circumferential flange on the attachment end of the arm 100, or by other well-known means of attachment. The tracker arm 100 may include opposing flats 101 that lie in planes parallel to the stylus and cannula flats 65, 75. In this manner, the stylus 60 and cannula 70 may be inserted into the inner tube of the handle base assembly 30 in a predetermined orientation relative to the opposing flats 101 of the tracker arm 100 and such that the stylus undercut 64 is in alignment with the pins 52.

The tracker arm 100 may include a striking plate 102 on a distal surface thereof. Such a plate may be a flat region stamped into the arm 100 that provides a greater surface area than the rest of the arm 100 along the distal portion of the arm with which to strike the arm and provide an impaction force in a proximal direction for use in separating the cannula from the other components of the navigable probe assembly 10, especially when the cannula is inserted into bone.

Figure 9:
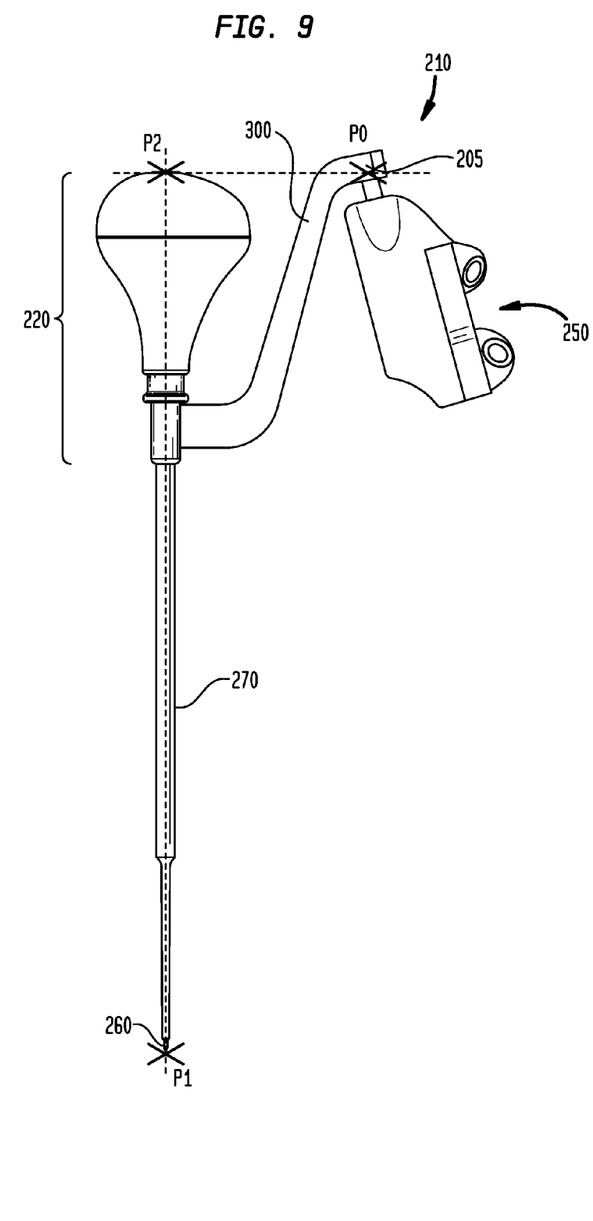
FIG. 9 is a side view of a navigable probe assembly in accordance with another embodiment.

On an end of the tracker arm 100 may be one or more posts 105 for connection with a tracking module, such as the tracking module 150 shown in FIG. 1 or the tracking module 250 shown in FIG. 9.

Referring to the configuration of FIGS. 5 and 6, in operation, when the cam 23 is rotated clockwise, an inner diameter of the cam along the longitudinal axes of the pins 52 of the locking mechanism 50 becomes increasingly smaller until the cam contacts the pins 52 to cause the pins 52 to slide in the direction of the longitudinal axes until the pins 52 are within or engaged with the respective stylus undercuts 64 and are thus in the locked position, as discussed previously herein. In contrast, when the cam 23 of the upper cap assembly 21 is rotated in the counterclockwise direction, the resilient element 54 may provide a force radially against the pin flanges 57 such that the pins 52 may be retracted to a position in which the pins 52 are not within or engaged with the stylus undercuts 64 and are thus in the unlocked position.

Referring to FIG. 7, in operation, the quick connect system 90 may be released by applying an axial force in the proximal direction, which may be applied by a user to collar flanges 96, to remove the radial load applied against cannula 70. As the cannula 70 is not fixed to the stylus 60, when quick connect system 90 is released and the locking mechanism is in the locked position, the stylus 60 may be slidingly separated from the cannula 70. In this manner, the handle assembly 20 engaged with the stylus 60 through the locking mechanism 50 (along with the tracker arm 100) may also be separated from the cannula 70. The stylus 60 may be separated from the locking mechanism 50, and thus the handle assembly 20, by placing the locking mechanism 50 in the unlocked position. In this manner, one stylus may be exchanged for a new or different stylus.

Still referring to FIG. 7, the impaction cap 53 of the locking mechanism 50 may have a physical hard stop 59 such that upon placement of the handle assembly 20 and locking mechanism 50 onto the stylus 60, the proximal most end of the stylus 60 abuts the physical hard stop 59 to set the relative position of the stylus 60 to the locking mechanism 50, and thus the relative axial position of the stylus undercuts 64 to the pins 52 and at least the tip at the stylus distal end 68 to the hard stop 59. An outer diameter of the stylus 60 may be substantially the same as a mating inner diameter of the inner tube 32 or the cannula 70 to set the relative radial position and orientation of the stylus 60 to the respective inner tube 32 or cannula 70. In this manner, a precise and repeatable position of the stylus with respect to a navigation tracking system, such as the tracker module 150 (as shown in FIG. 1), may be established.

The inner tube 32 of the handle base assembly 30 may have a physical hard stop 36 such that, upon placement of the handle assembly 20 onto the cannula 70, a step 73 (as best shown in FIG. 4B) located at the proximal end 72 of, or in the alternative the proximal most end of, the cannula abuts the physical hard stop 36 to set either or both of an engagement length of the handle base assembly 30, including the quick connect system 90, with the cannula 70 and the relative axial position of at least the tip 84 at the cannula distal most end 82 to the hard stop 36. An outer diameter of the cannula 70 may be substantially the same as a mating inner diameter of the inner tube 32 to set the relative radial position and orientation of the cannula 70 to the inner tube 32. In this manner, a precise and repeatable position of the cannula with respect to a navigation tracking system, such as the tracking module 150 (as shown in FIG. 1), also may be established. Due to the use of the physical hard stops 36 and 59, upon complete assembly of the navigable probe 10, a user may strike the impaction cap 53 to facilitate insertion of the stylus 60 and cannula 70 into bone.

Figure 10:
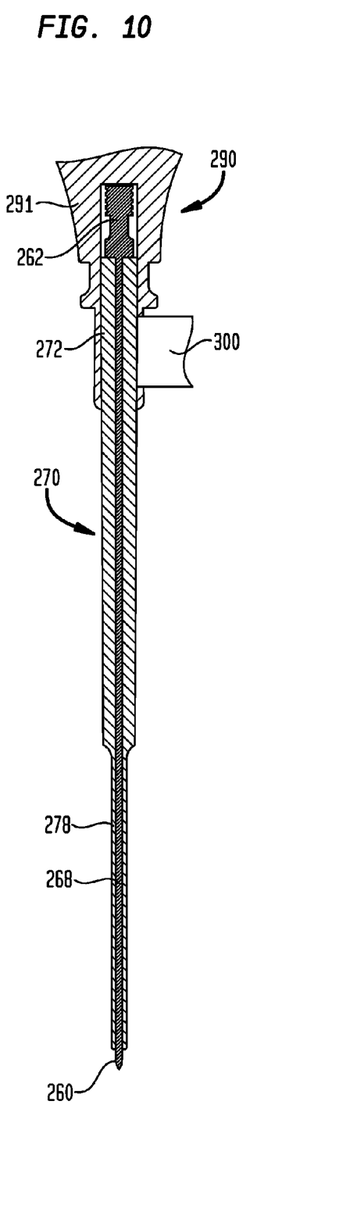
FIG. 10 is a cross-sectional side view of a portion of the navigable probe assembly of FIG. 9.

FIGS. 9 and 10 illustrate an alternative arrangement of a navigable probe 210. As shown, the navigable probe 210 may include a handle assembly 220, stylus 260, cannula 270, and tracker arm 300 having tracking posts 205 connected with the tracking module 150. As further shown, in some arrangements of the navigable probe 210, the handle assembly 220 may not include a locking mechanism therein. Instead, as shown in FIG. 10, a proximal end 262 of the stylus 260 as well as proximal end 272 of the cannula 270 may be inserted into a cavity of a collar 291 that is part of a quick connect system 290 (not fully shown) at a distal end of the handle assembly 220. In this manner, the stylus 260 and the cannula 270 may be separated from the handle assembly 220 when the quick connect system 290 is released but may be fixed, or at least non-rotational, with respect to the handle assembly 220 when the quick connect system 290 is engaged with, i.e. compressed against, the cannula 270. Distal ends 268, 278 of the stylus 260 and cannula 270 may have similar configurations to the distal ends 68, 78 of the stylus 60 and cannula 70 of the navigable probe 10.

Referring again to FIG. 9, an end of the tracker arm 300 may be set at a point P0 that is along a radius drawn from a point P2 set at the proximal most end of the navigable probe 210. Moreover, the distal most point of the navigable probe 210, identified as point P1, may be set at a nominal distance of 7 inches, which is preferably in a range between 5 inches and 9 inches, from the distal most end of the collar 291 of the quick connect system 290. In this manner, the relative distances of the points P0, P1, and P2 remain fixed such that the tracking module 150 can repeatably and reliably detect the position and orientation of the navigable probe assembly 10 due to the fixed relative positions of the components of the assembly 10.

In use, in accordance with an embodiment, a cannula 70 of a navigable probe assembly 10 may be inserted through the skin of a patient. The cannula 70 may have a larger diameter through most of the distal end 80 and act as a dilator as it enters through the skin of the patient. After passing the cannula 70 through the skin a predetermined depth at a predetermined orientation as determined by a calibrated tracking module 150 extending from the navigable probe assembly, as described in the '114 patent, which may be a depth determined prior to or during a surgery, a distal end 68 of a stylus 60 located within the tapered distal end 82 of the cannula 70 of the navigable probe assembly 10 may be inserted into the spine or other bone of a patient. In general, a user may strike a proximal surface of an impaction cap 53 exposed on a proximal end of a handle assembly 20 in order to supply the necessary force to insert. A rounded, ergonomic shape of the handle assembly 20 of the navigable probe assembly 10 may provide a smooth surface on which to press the navigable probe assembly 10 through the skin and into the spine of the patient.

Prior to or during insertion of the navigable probe assembly 10, the upper cap assembly 21 of the probe assembly 10 may be rotated to a "locked position" to cause a cam 23 that may be located within the handle assembly 20 to rotate a corresponding angle of rotation. The cam 23 may have a varying diameter such that, upon rotation of the upper cap assembly 21 to the locked position, a diameter of the cam 23 that is relatively smaller than the rest of the cam 23 causes pins 52 of a locking mechanism 50 to move toward the center of the cam 23 and become engaged with the stylus 60 of the probe assembly 10.

Due to the engagement of the respective flats 65, 75 of the stylus 60 and the cannula 70 with the respective portions of the respective flats 34 of the inner tube 32 of the handle assembly 20, rotation of the handle assembly 20 may transmit a corresponding angular rotation to the stylus 60 and the cannula 70 such that a rotation of the handle assembly 20 by the user has a corresponding rotation of the stylus 60 and the cannula 70, allowing the user to control the angular movement of the stylus 60 and the cannula 70. As the distal end 68 of the stylus 60 may have a tapered blade thereon, and the cannula 70 may have cutting flutes or other non-cylindrical features (not shown), such control of the stylus 60 and the cannula 70 can enhance the ability of the user of the navigable probe assembly 10 to cut through bone.

After the stylus 60 and the cannula 70 are embedded into the body to a predetermined depth, in some arrangements, a user may disengage the stylus 60 and the other components of the probe assembly 10 from the cannula 70 when the upper cap assembly 21 of the probe assembly 10 is in "locked position" by releasing the quick connect system 90 and by pulling the probe assembly 10 with the stylus 60 engaged thereto such that the stylus 60 may slide axially in the proximal direction through the inner diameter of the cannula 70. In this manner, the cannula 70 alone may remain in the bone. In such a configuration, a K-Wire (not shown) may be inserted into the inner diameter of the cannula 70 and further may be advanced into the bone to mark the cannula and stylus trajectory and to serve as a guide for subsequent steps in the procedure.

After the stylus 60 and the cannula 70 are embedded into the body to a predetermined depth, or the stylus 60 and the probe assembly 10 are disengaged from the cannula 70, a user may rotate the upper cap assembly 21 to an "unlocked" position to cause the cam 23 to rotate a corresponding angle of rotation. Upon such rotation, the diameter of the cam 23 that is relatively larger than the rest of cam 23 may provide a space for the pins 52 to move outwardly from the center of the cam 23. One or more springs of the locking mechanism 50 may be compressed against pin flanges 57 on the pins 52 such that as the cam 23 rotates to provide a space for the pins 52 to move, the one or more springs push the pins 52 outwardly from the center of the cam 23 such that the pins 52 remain against the changing diameter of the cam 23. As the pins 52 reach a predetermined radial position from the center of the cam 23 as they move outwardly from the center of the cam 23, the pins 52 may disengage from undercuts 64 of the stylus 60. In this manner, when the pins 52 become disengaged from the stylus 60, the stylus 60 may be removed from the navigable probe assembly 10 in the absence of other restrictions, such as constriction in some arrangements that may be caused by a quick connect system, as described further herein. The ability to disengage the cannula 70 and the stylus 60 from the probe assembly 10 provides an option to leave the stylus 60 inside the cannula 70 while embedded in the bone, allowing for one or both of intra-operative fluoroscopy images to be produced and photos to be taken along the longitudinal axis of the cannula 70 without interference from the probe assembly 10. Subsequently, the probe assembly 10 may be reattached to the cannula 70, and also may be reattached to the stylus 60, to continue the procedure.

In some arrangements in which the cannula 70 is connected to a handle base assembly 30 of a handle assembly 20 by a quick connect system, such as the quick connect system 90, the quick connect system 90 may be operated by sliding a collar 91 axially to release the cannula 70 which may then be separated from the handle assembly 20. In some arrangements, such separation of the cannula 70 may allow a second dilator having an inner diameter larger than the outer diameter of the original dilator to be slid over the original dilator, whether with or without the stylus 60 or K-wire inserted, without assistance from the navigation tracking system. The option of sliding the larger diameter dilator over the cannula 70 and the stylus 60 is possible due to the fact that the shapes of the exteriors of both the cannula 70 and the stylus 60 are bound by a predetermined outer diameter that is smaller than an inner diameter of the larger dilator. Due to the larger diameter of the second dilator, the user may further enlarge or dilate the incision produced by the original cannula. By serving the function of the initial dilator, the cannula 70 may save a surgical step of removing the cannula 70 and replacing the cannula 70 with the initial dilator.

In the example of navigated probe assembly 10, when the pins 52 are disengaged from the stylus 60, removal of the cannula 70 may permit the stylus 60 to also be removed from the handle assembly 20. After removing the stylus, the user may later reinsert one or both of the original stylus 60 and the cannula 70 or may replace one or both of the original stylus 60 and the cannula 70 with one of both of a second stylus and a second cannula, respectively. The tracking module 150 may then be recalibrated with one or both of the second stylus and the second cannula such that the tracking module 150 can repeatably and reliably detect the position and orientation of the navigable probe assembly 10 with one or both of the second stylus and the second cannula inserted. Moreover, through control of precise dimensions of the stylus and cannula during manufacturing thereof, the original calibration parameters of the tracking module 150 may remain valid and the recalibration step may be avoided.

In some arrangements (not shown), with the stylus removed from the handle assembly, an instrument or portion of an instrument, such as but not limited to a drill bit, a needle for one or both of aspirating bone and delivering bone cement, a neuromonitoring probe, and an ultrasound probe (including but not limited to a Doppler type of the ultrasound probe) may be inserted and removed through the aperture 61 in the impaction cap 53 and the inner tube 32 of the handle assembly 20, and in some arrangements, further through the cannula 70. Additionally, in some arrangements (not shown) with the stylus inserted in the handle assembly, a neuromonitoring cable or a neuromonitoring connected may be passed through the aperture of the impaction cap and connected to the stylus. Additionally, in other arrangements (not shown), with the stylus 60 and the cannula 70 removed, an instrument or a portion of an instrument, such as but not limited to a drill guide, a probe or a needle-specific cannula, an awl, end plate preparation instruments and interbody device insertion instruments can be inserted through the distal end of the probe assembly. In some arrangements, these instruments may be configured to be engaged with one or both of the locking mechanism 50 and the quick connect system 90.

It is to be understood that the disclosure set forth herein includes all possible combinations of such particular features. For example, where a particular feature is disclosed in the context of a particular aspect, arrangement, configuration, or embodiment, or a particular claim, that feature can also be used, to the extent possible, in combination with and/or in the context of other particular aspects, arrangements, configurations, and embodiments of the invention, and in the invention generally.

Furthermore, although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A navigable probe for providing a trajectory for insertion of and for tracking the position of surgical tools comprising:
    a handle assembly including a lower handle, an upper cap rotatable relative to the lower handle between locked and unlocked positions, and a locking mechanism enclosed by the upper cap and the lower handle:
    a cannula disposed within and removably connected to the handle assembly; and
    a stylus disposed within the cannula and removably connected to the handle assembly,
    wherein the locking mechanism of the handle assembly has locked and unlocked positions corresponding to the upper cap locked and unlocked positions, wherein upon rotation of the upper cap to the upper cap locked position, the locking mechanism is in the locked position, and the upper cap presses at least a portion of the locking mechanism into the stylus whereby the locking mechanism contacts the stylus to prevent axial movement of the stylus relative to the handle assembly, and, in the unlocked position, the locking mechanism disengages the stylus to allow for axial movement of the stylus relative to the handle assembly, and
    wherein the axial movement of the stylus is prevented by the locking mechanism without preventing axial movement of the cannula when the locking mechanism is in the locked position.

2. The navigable probe of claim 1, further comprising a tracking module connected to the handle assembly, the tracking module being fixed in position relative to at least one of the cannula and the stylus, wherein the tracking module detects at least one of position and orientation of the navigable probe.

3. The navigable probe of claim 2, the tracking module being connected to the handle assembly by an arm, wherein an impaction surface of the arm is flat to provide for an impaction force over an area of the impaction surface against a body tissue during removal of the cannula from the handle assembly.

4. The navigable probe of claim 1, wherein in the locked position of the locking mechanism, at least one pin of the locking mechanism is disposed in a corresponding undercut defined by the stylus, and wherein in the unlocked position of the locking mechanism, the at least one pin of the locking mechanism is not disposed in the corresponding undercut defined by the stylus.

5. The navigable probe of claim 1, further comprising a quick connect system removably fixing the cannula to the handle assembly, the quick connect system being adjustable between first and second positions,
    wherein, when the quick connect system is in the first position, the cannula is fixed in position relative to the handle assembly, and
    wherein, when the quick connect system is in the second position, the cannula is movable relative to the handle assembly.

6. The navigable probe of claim 5, the cannula and the stylus being slideably engaged with each other,
    wherein, when the quick connect system is in the first position, the cannula is fixed in position relative to the stylus, and
    wherein, when the quick connect system is in the second position, the stylus is slideable along the cannula.

7. The navigable probe of claim 5,
    wherein, when the quick connect system is in the second position and the locking mechanism is in the unlocked position, both the handle assembly and the stylus are removable from the cannula.

8. The navigable probe of claim 7, wherein the handle assembly and the stylus are fixed such that the stylus is not axially movable relative to the handle assembly.

9. The navigable probe of claim 5, the quick connect system including a collar having at least a portion movable between first and second positions along a portion of the handle assembly in a direction parallel to a longitudinal axis of the cannula, a compression element compressible between the handle assembly and the collar, and a locking element held between the collar and the cannula,
    wherein, when the collar is in a first position, the compression element compresses the collar against the locking element to cause the locking element to be compressed against the cannula such that the position of the cannula relative to the handle assembly is fixed, and
    wherein, when the collar is in the second position, the locking element is in a state such that the handle assembly and the cannula are slideable relative to each other.

10. The navigable probe of claim 9, wherein the collar has a taper such that, when the collar is in the first position, the taper contacts the locking element to cause the compression of the cannula for maintaining the position of the cannula relative to the handle assembly.

11. The navigable probe of claim 10, wherein the locking element is ball-shaped.

12. The navigable probe of claim 1,
    wherein the locking mechanism includes pins insertable into a proximal end of the stylus and a resilient element attached to the pins,
    wherein, the upper cap includes a cam such that upon rotation of the upper cap to the locked position, the cam presses at least a portion of the pins into the proximal end of the stylus to prevent axial movement of the stylus relative to the handle assembly, and
    wherein, upon rotation of the upper cap to the unlocked position, the resilient element supplies a force against the pins to retract the pins from the stylus.

13. The navigable probe of claim 12, wherein the resilient element is a leaf spring compressed between flanges extending radially from each of the pins, the leaf spring supplying the force to the flanges of the pins.

14. The navigable probe of claim 1, wherein the handle assembly includes at least one tube extending along a distal portion thereof coaxially with the cannula and the stylus passing through a lumen thereof, wherein the stylus includes at least one flat stylus surface at a proximal end thereof and the cannula includes at least one flat cannula surface at a proximal end thereof, and wherein the at least one tube has at least one flat inner surface along at least a portion thereof for mating engagement with each of the flat stylus surface and the flat cannula surface such that, when the flat stylus surface and the flat cannula surface are in mating engagement, rotation of at least one of the cannula and the stylus relative to the handle assembly is prevented.

15. A probe for providing a trajectory for insertion of surgical tools comprising:
 a handle assembly including a lower handle, an upper cap assembly having an upper cap and a cam fixed thereto and being rotatable relative to the lower handle, and a locking mechanism enclosed by the upper cap assembly and the lower handle;
 a cannula disposed within and removably connected to the handle assembly; and
 a stylus disposed within the cannula and removably connected to the handle assembly,
 wherein the locking mechanism includes pins insertable into the stylus and a resilient element attached to the pins,
 wherein, upon rotation of the upper cap assembly to a locked position, the cam presses at least a portion of the pins into the proximal end of the stylus such that the stylus is fixed in position relative to the handle assembly, and
 wherein, upon rotation of the upper cap assembly to an unlocked position, the resilient element supplies a force against the pins to retract the pins from the stylus.

* * * * *